United States Patent
Miller et al.

(10) Patent No.: US 11,998,190 B2
(45) Date of Patent: Jun. 4, 2024

(54) METHOD AND APPARATUS FOR SERIAL DEPLOYMENT OF MULTIPLE TISSUE FASTENERS

(71) Applicants: Arnold Miller, Cambridge, MA (US); Raanan Miller, Cambridge, MA (US)

(72) Inventors: Arnold Miller, Cambridge, MA (US); Raanan Miller, Cambridge, MA (US)

(73) Assignee: Amsel Medical Corporation, Cambridge, MA (US)

( * ) Notice: Subject to any disclaimer, the term of this patent is extended or adjusted under 35 U.S.C. 154(b) by 138 days.

(21) Appl. No.: 15/447,747

(22) Filed: Mar. 2, 2017

(65) Prior Publication Data

US 2017/0202551 A1 Jul. 20, 2017

Related U.S. Application Data

(63) Continuation-in-part of application No. 15/380,245, filed on Dec. 15, 2016, now abandoned, and a
(Continued)

(51) Int. Cl.
*A61B 17/064* (2006.01)
*A61B 17/00* (2006.01)
(Continued)

(52) U.S. Cl.
CPC ...... *A61B 17/064* (2013.01); *A61B 17/00008* (2013.01); *A61B 17/0682* (2013.01);
(Continued)

(58) Field of Classification Search
CPC .............. A61B 17/0057; A61B 17/064; A61B 17/0643; A61B 17/068; A61B 17/0682; A61B 17/0686; A61B 17/072; A61B 17/08; A61B 17/083; A61B 17/10; A61B 17/12; A61B 17/12009; A61B 17/12013; A61B 17/12022; A61B 17/12027; A61B 17/12031; A61B 17/12036; A61B 17/1214; A61B 17/12145; A61B 17/122; A61B 17/128; A61B 17/1285; A61B 2017/00575; A61B 2017/00641; A61B 2017/00646; A61B 2017/00668; A61B 2017/00986; A61B 2017/0419; A61B 2017/0641; A61B 2017/0645; A61B 2017/088; A61B 2017/0867; A61B 2017/12018; A61B 2017/1205; A61B 2017/12054; A61B 2017/12095; A61B 2017/00893; A61B 2017/00871; A61B 2017/00867;
(Continued)

(56) References Cited

U.S. PATENT DOCUMENTS

2004/0044364 A1* 3/2004 DeVries ............... A61B 17/064
606/213
2005/0267524 A1 12/2005 Chanduszko
(Continued)

*Primary Examiner* — Jocelin C Tanner
(74) *Attorney, Agent, or Firm* — Bookstein IP Law

(57) ABSTRACT

One-piece tissue fasteners are provided for securing two or more tissue layers to each other. Delivery devices are described by which a tandem array of such fasteners can be delivered and deployed to secure tissue layers in a number of locations without requiring removal or reloading of the removal tool.

9 Claims, 8 Drawing Sheets

Related U.S. Application Data continuation of application No. 15/226,577, filed on Aug. 2, 2016, now abandoned, and a continuation of application No. 13/348,416, filed on Jan. 11, 2012, now abandoned.

(60) Provisional application No. 62/303,071, filed on Mar. 3, 2016.

(51) Int. Cl.

| | | |
|---|---|---|
| *A61B 17/04* | (2006.01) | |
| *A61B 17/068* | (2006.01) | |
| *A61B 17/12* | (2006.01) | |
| *A61B 17/122* | (2006.01) | |
| *A61B 17/128* | (2006.01) | |

(52) U.S. Cl.
CPC ........ *A61B 17/12* (2013.01); *A61B 17/12009* (2013.01); *A61B 17/12013* (2013.01); *A61B 17/12022* (2013.01); *A61B 17/12027* (2013.01); *A61B 17/12031* (2013.01); *A61B 17/12036* (2013.01); *A61B 17/1214* (2013.01); *A61B 17/12145* (2013.01); *A61B 17/122* (2013.01); *A61B 17/128* (2013.01); *A61B 17/1285* (2013.01); *A61B 2017/00668* (2013.01); *A61B 2017/00867* (2013.01); *A61B 2017/00893* (2013.01); *A61B 2017/00986* (2013.01); *A61B 2017/0419* (2013.01); *A61B 2017/0641* (2013.01); *A61B 17/0643* (2013.01); *A61B 2017/0645* (2013.01); *A61B 2017/12054* (2013.01); *A61B 2017/12095* (2013.01)

(58) Field of Classification Search
CPC ........ A61B 17/12109; A61B 17/12099; A61B 17/00008
USPC .................. 606/143, 151, 157, 158, 213
See application file for complete search history.

(56) References Cited

U.S. PATENT DOCUMENTS

| | | | |
|---|---|---|---|
| 2005/0267529 | A1 | 12/2005 | Chanduszko |
| 2009/0326578 | A1* | 12/2009 | Ewers ................ A61B 17/0401 606/213 |
| 2011/0092877 | A1* | 4/2011 | Brenneman ............ A61B 17/11 604/8 |

* cited by examiner

METHOD AND APPARATUS FOR SERIAL DEPLOYMENT OF MULTIPLE TISSUE FASTENERS

FIELD

This disclosure relates to apparatus and methods to apply one-piece tissue fasteners to tissue layers to secure the layers together and to delivery devices for such fasteners by which multiple fasteners can be serially deployed without requiring removal and reloading of the delivery device.

BACKGROUND

Among the many methods and devices for securing tissue such as, suturing, hemostatic clips, staples, and adhesives some delivery devices are capable of delivering multiple clips, staples and the like, serially, without requiring removal and reloading of the delivery tool. It is among the objects of the invention to provide improved one-piece fasteners and to provide an improved, simplified device and method for delivering a series of one-piece tissue fasteners to fixate tissue layers.

SUMMARY

The tissue fasteners of the present invention may be formed as a single piece and a plurality of such fasteners can be loaded in a tandem array into a tubular delivery device such as a needle. Each fastener may be in the form of a tubular body with proximal and distal ends and having legs extending from each of the ends. The fasteners may be formed from a shape memory material so that the legs can be folded to a low profile in which they can be contained in the lumen of the delivery needle. When released from the containment of the delivery needle the legs self-expand to a deployed configuration in which they extend radially outward of the axis of the tubular body. The fasteners are deployed by first advancing the pre-loaded delivery tube or needle through the layers of tissue. With the distal end of the needle beyond the distal tissue layer, the leading fastener is advanced out of the needle to expose and release the constraint on the distal legs of the fastener so that the distal legs self-deploy. While maintaining the position of the leading fastener, the needle then is retracted proximally to expose and release the constraint on the proximal legs such that the tissue layers are secured between the deployed proximal and distal legs. Mechanisms are provided for advancing and deploying the fasteners in sequence.

DRAWINGS

The various objects and advantages of the invention will be appreciated more fully from the following description and accompanying drawings in which.

ILLUSTRATIVE EMBODIMENTS

FIG. 1 shows an embodiment of a one-piece fastener 10 as may be used in the practice of the invention. The fastener 10 has a tubular body 12 with proximal and distal ends 14, 16 and proximal and distal legs 18, 20 extending form the ends of the body 12. The fastener 10 preferably is formed from shape memory material such as Nitinol alloy and may be formed by laser cutting from a tube as is well known in the art. After cutting the fastener is heat-treated to its intended configuration to have a relaxed, unstressed, shape as shown, in which the legs extend generally radially outward about the body. Although, in the illustrative embodiment the fastener is shown as having three proximal and three distal legs, fasteners may be made with as few as two or as many as five legs. The alloy should be selected so that the legs 18, 20 can be folded to a stressed, more longitudinally extending position so that the fasteners can be disposed within the lumen of a delivery tube, in tandem, as described below. Upon release from the delivery tube the legs self-expand to their radially extended, deployed configuration.

Figure 1A:
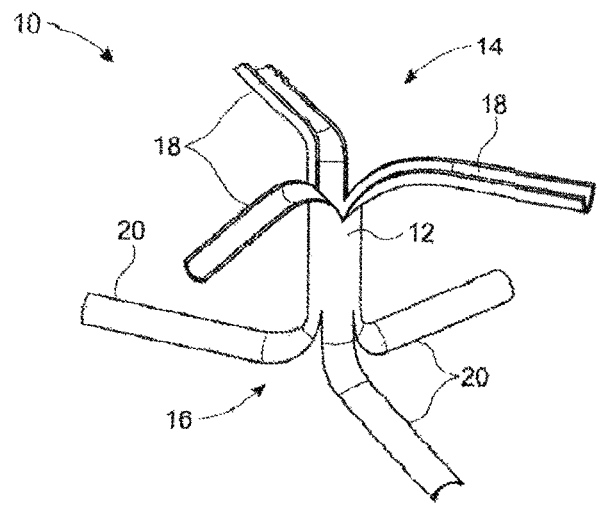
FIG. 1A is an isometric illustration of an embodiment of a one-piece fastener in a relaxed, unstressed configuration as may be employed in the practice of the invention.
Figure 1B:
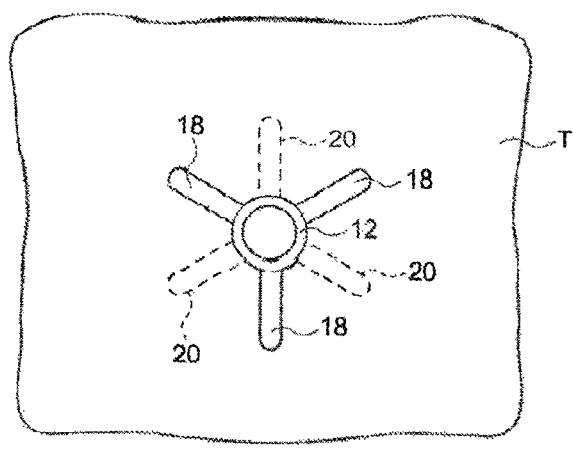
FIG. 1B is a plan view of the fastener of FIG. 1A in engagement with layers of tissue.
Figure 1C:
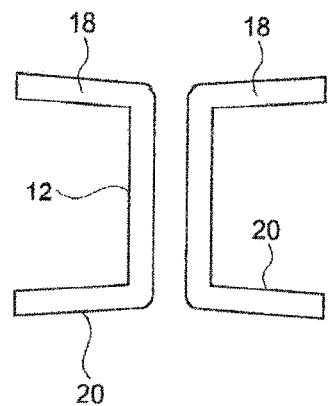
FIGS. 1C-1E are diagrammatic illustrations of various configurations of the legs of embodiments of the fastener.

FIG. 1B illustrates, in plan, the manner in which the fastener embodiment of FIG. 1A engages tissue T. In this embodiment the fastener has three proximal and three distal legs that are arranged to be out of registry with each other. The legs of each overlie the spaces between the legs of the other. With this arrangement, when the fastener is deployed with tissue layers contained between the proximal and distal legs, the legs apply alternately, oppositely directed forces to opposite surfaces of the tissue layers. The proximal legs will apply force to the tissue in a distal direction and the distal legs will apply force in a proximal direction. These forces alternate circumferentially about the center of the fastener and, depending on the length of the tubular body 12 and the thickness and characteristics of the tissue, may constrain the tissue layers in serpentine configuration. In this embodiment of fastener the legs 18, 20, when unstressed, extend substantially perpendicular to the axis of the tubular body as shown, diagrammatically, in FIG. 1C.

Figure 1D:
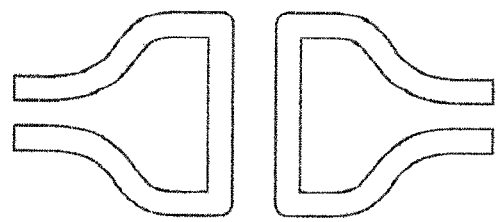
Figure 1E:
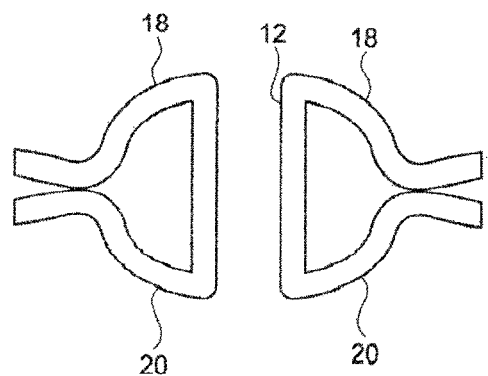

The legs 18, 20 may have other configurations as shown, for example, in diagrammatic FIGS. 1D and 1E. In FIG. 1D the free ends of the legs in each group are angled toward the opposite end of the body 12 so that they will effect a more pronounced shape to the constrained tissue layers. That effect may be extended even further as shown in FIG. 1E in which the free ends of the unstressed proximal and distal legs cross each other in an interdigitated configuration with the tissue being constrained in a serpentine pattern extending circumferentially about the fastener. It should be understood, however, that aspects of the invention may be practiced with other configurations of one-piece fasteners, for example, in which the proximal and distal legs are in registry with each other.

FIGS. 2A-2I illustrate the delivery device and the sequence of steps in the delivery of multiple fasteners. The delivery device includes an elongate delivery tube, such as a needle 22, having a distal outlet opening 24 and a sharp tip 26. For use in a laparoscopic procedure the distal tip may be blunt. A number of fasteners 10 are pre-loaded into the lumen 28 of the needle, in tandem, with their proximal and distal legs stressed into a more longitudinally extended low profile configuration. The tips of the legs engage the luminal surface of the needle frictionally but can be made to slide within the needle. The delivery device also includes a shuttle mechanism, indicated generally at 30, by which the position of the leading fastener relative to the needle can be controlled.

Figure 2A:
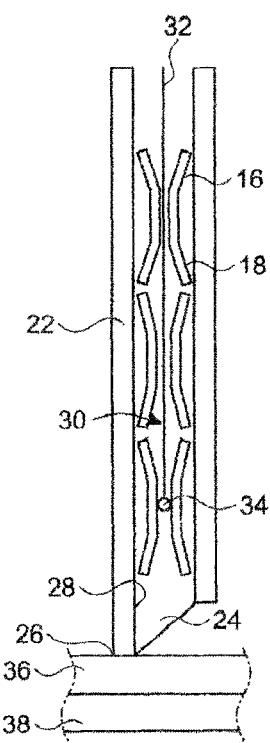
FIGS. 2A-2I are sequential illustrations of a manner in which the fasteners are delivered and deployed in accordance with one embodiment of the invention.
Figure 2B:
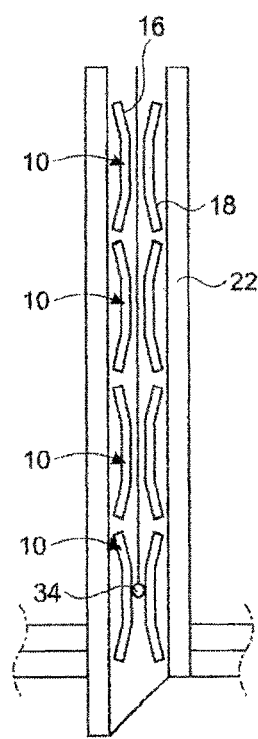
Figure 2C:
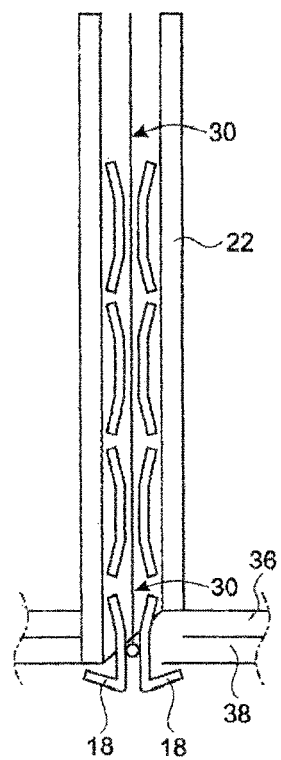
Figure 2D:
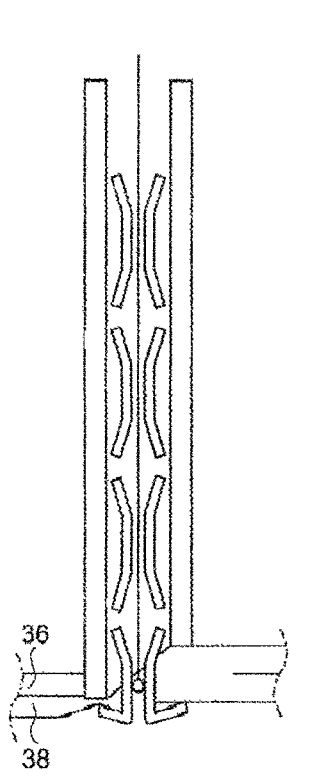
Figure 2E:
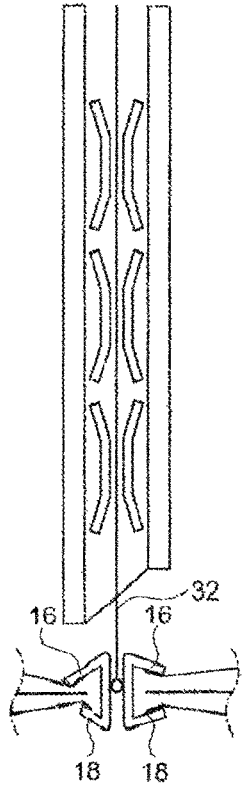
Figure 2F:
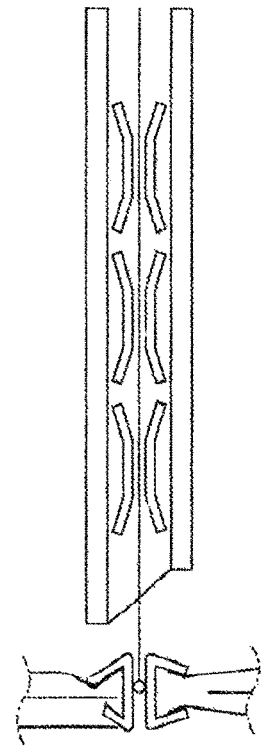
Figure 2G:
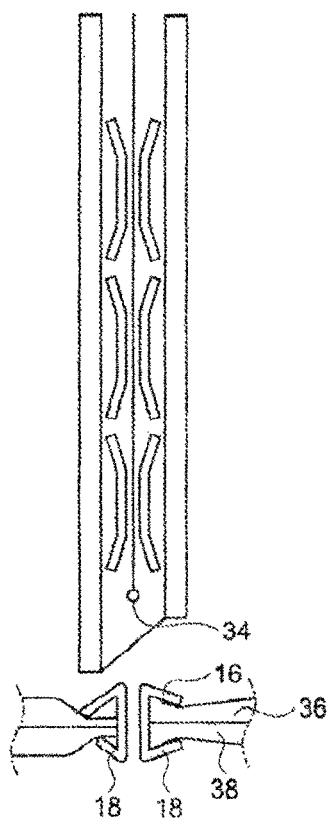
Figure 2H:
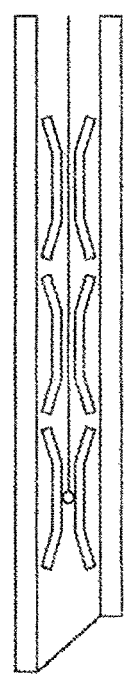
Figure 2I:
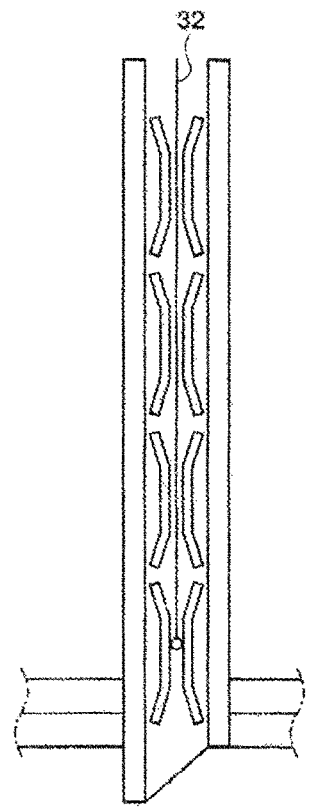

FIGS. 2A-2I illustrate operation of one embodiment of a shuttle mechanism that includes a shaft 32 with an expandable member 34 at its distal end. In this embodiment the shaft may have a lumen (not shown) and the expandable member may be in the form of a balloon or similar component that can be expanded and contracted selectively. The expandable member 34 is adapted to engage the lumen within the tubular body 12 of the fastener 10 sufficiently to cause the fastener to slide within the needle lumen 28 upon relative movement of the shaft and needle. The sequence of steps in the deployment of a fastener begins as in FIG. 2A which shows the expandable member disposed and inflated within the body of the leading fastener. The needle is advanced into and through the tissue layers 36, 38 (FIG. 2B) so that the outlet opening 24 is just beyond the most distal tissue layer 38. The tissue layers may comprise the opposing walls of a body lumen such as a blood vessel (as to occlude the vessel) or tissue layers in other parts of the body. The shuttle mechanism 30 then is advanced to urge the distal legs 20 of the leading fastener out of the needle on the distal side of the tissue. With the distal legs 20 released from the constraint of the delivery tube, the distal legs self-deploy to their expanded configuration. At this point in the procedure the clinician can retract the distal portion of the fastener back into the delivery tube by retracting the shaft 32 if it is determined that the initial placement was not as originally intended. The needle then can be repositioned and the deployment continued. Once it is determined that the placement is acceptable (FIGS. 2C, 2D), the position of the fastener is maintained by the shuttle mechanism 30 and the needle is retracted to uncover and release the proximal legs 18 to expand to their deployed configuration (FIG. 2E). The expandable member 34 then can be deflated and the needle then can be moved to another tissue location. The expandable member is again positioned in the new leading fastener and is expanded in readiness for the next deployment.

Figures 3A, 3B, 3C:
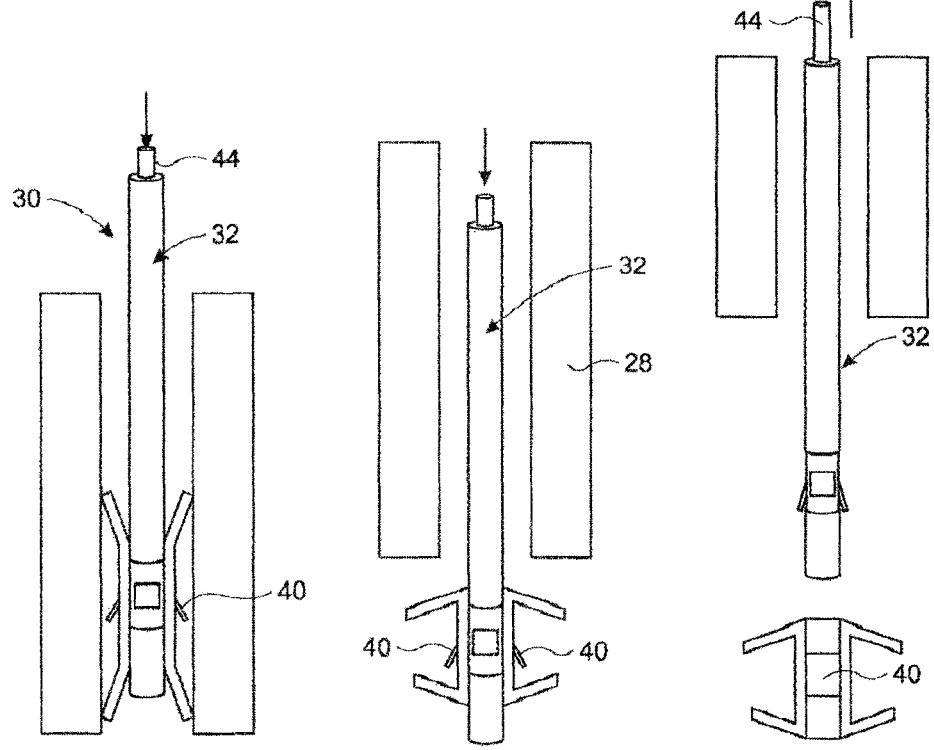
FIGS. 3A-3C illustrate another embodiment of the mechanism for deploying the fasteners.

FIGS. 3A-3C illustrate another embodiment of a shuttle mechanism 30 in which the shaft 32 is hollow and contains, at its distal end, detents 40 that can project laterally selectively to engage sockets 42 formed in the tubular wall of the fastener bodies 12. Operation of the detents 40 is controlled by an actuator rod 44 that extends through a lumen in the shaft 32 and is mechanically connected to the detents to extend them or to retract them. FIG. 3B shows detents 40 in secure engagement with the fastener sockets. FIG. 3C shows the fastener released from the detents. The sequence of deployment is the same as discussed above.

Figure 4A:
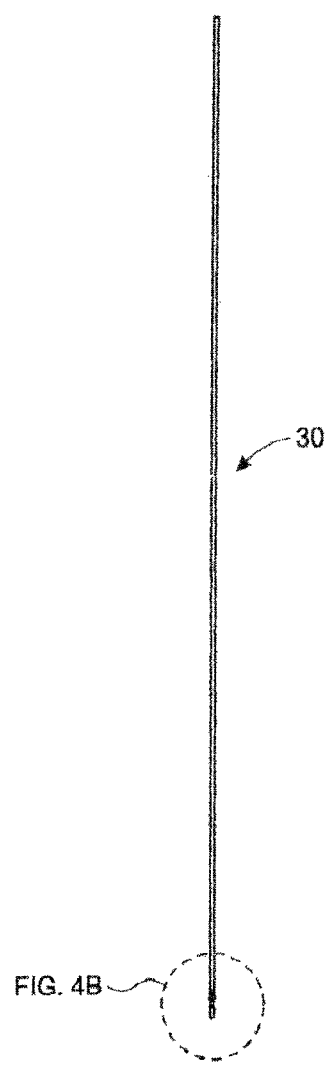
FIGS. 4A and 4B are illustrations of another embodiment of a mechanism for deploying the fasteners.
Figure 4B:
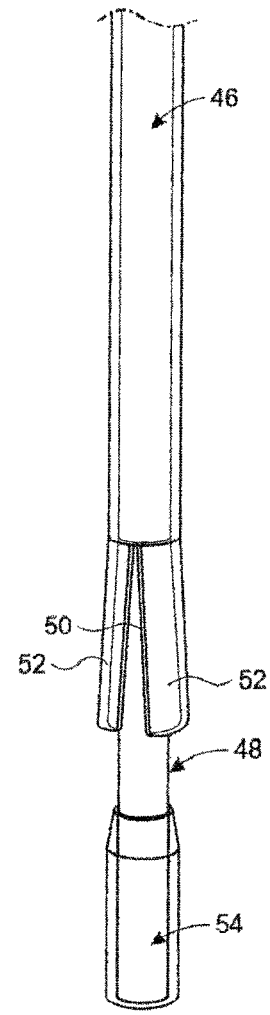

FIGS. 4A and 4B illustrate another embodiment of shuttle mechanism 30 in which the shaft has an outer tube 46 and an inner actuator rod 48 slidable within the tube 46. The distal end of the actuator rod extends beyond the distal end of the outer tube. The distal end of the tube 46 has a number of slits 50 that define legs 52 that can be spread apart in a radial direction. The legs 52 are biased inwardly but can be spread apart by an enlargement 54 formed at the distal end of the actuator rod 48. The legs 52 can be urged against the interior of the tubular body to control the position of the fastener in the deployment sequence as described above.

Figure 5:
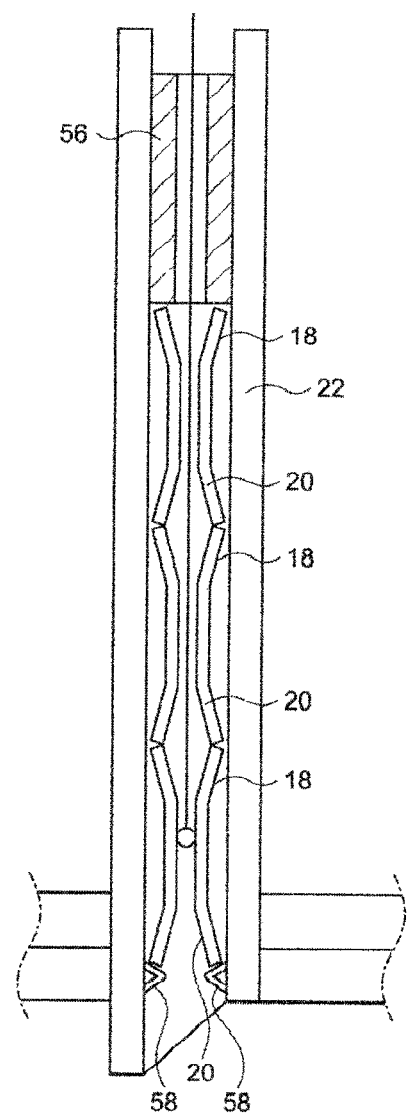
FIG. 5 is a diagrammatic illustration of another embodiment of a mechanism for deploying the fasteners.

FIG. 5 illustrates another manner by which the fasteners can be deployed. In this embodiment, the tandem fasteners 10 are arranged end-to-end with the tips of the proximal legs 18 of each fastener in contact with tips of the distal legs 20 of the immediately trailing fastener so enable the column to be moved distally in unison, as a unit. A pushing member such as a rod or tube or spring 56 may be disposed behind the most trailing fastener and is slidable in the delivery tube 22 in order to advance the column of tandem fasteners. The distal end of the delivery tube 22 may be provided with a detent mechanism 58 on the interior of the tube 22 to engage leading fastener. The detent serves to hold the leading fastener in position to be deployed as described above but can be overcome as the leading fastener is advanced. From engagement with the detent 58, the shuttle mechanism or the pusher 56 can deploy the leading fastener. With this embodiment the shuttle mechanism 30 can be used to maintain the position of the leading fastener while retracting the delivery tube or to engage a partially deployed fastener to draw it back into the delivery tube.

From the foregoing, it will be appreciated that the invention provides simple and effective tissue fasteners as well as methods and devices for securing at least two tissue layers together and by delivering multiple fasteners to attachment sites without requiring removal and reloading of the delivery device.

It should be understood, however, that the foregoing description is intended merely to be illustrative and that other embodiments, modifications and equivalents may become apparent to those skilled in the art with out departing from the principles of the invention.

The invention claimed is:

1. A system for delivering and deploying a plurality of tissue fasteners to multiple locations of tissue layers to be secured to each other comprising:
   a delivery tube having proximal and distal ends and having a lumen and a distal outlet opening at the distal end; a plurality of tissue fasteners disposed in a tandem array in the lumen of the delivery tube, each of the tissue fasteners comprising a tubular body having proximal and distal ends and an inner lumen
   a shuttle mechanism extending through the delivery tube and through bodies of the tandem fasteners, the shuttle mechanism being movable longitudinally within the delivery tube, the shuttle mechanism having at its distal end, a a fastener-engaging mechanism for selectively engaging a fastener body within the lumen of the fastener sufficiently to slide the fastener within the lumen of the delivery tube in a distal or proximal direction;
   whereby the shuttle mechanism may selectively eject the most distal of the fasteners in the array within the delivery tube toward and out of the distal outlet or retract a partially ejected fastener back into the delivery tube.

2. The system as defined in claim 1 in which the shuttle mechanism is retractable within the delivery tube to selectively engage the next leading fastener in the tandem array.

3. The system as defined in claim 1 wherein the delivery tube comprises a needle having a sharp tip.

4. The system as defined in claim 1 wherein the shuttle mechanism comprises an elongate shaft and where the fastener-engaging mechanism for selectively engaging a fastener comprises a radially expandable member selectively expandable to engage a luminal portion of a fastener body to enable movement of the fastener within and out of the delivery tube.

5. The system as defined in claim 4 where the radially expandable member comprises a balloon.

6. The system as defined in claim 4 wherein each of the fasteners has a detent element formed in its body and the fastener-engaging mechanism comprises a detent element disposed at the distal end of the shaft and being selectively engageable with the detent elements on the fastener bodies; and an actuator rod extending through the shaft and operatively engaged with the detent elements of the shaft for selectively operating the shaft detent element.

7. The system as defined in claim 4 where the expandable member comprises: the shaft having an outer tube an inner actuator rod that extends distally of the distal end of the outer tube, the distal end of the outer tube having a plurality of longitudinal slits that define a plurality of radially expandable legs, the actuator rod having an enlarged distal end that can selectively engage the distal ends of the legs to expand or contract the effective diameter.

8. The system as defined in claim 1 wherein the fasteners are disposed in the delivery tube in a column in end-to-end engagement with each other and further comprising: a pushing member disposed within the delivery tube in engagement with the most trailing fastener in the column.

9. The system as defined in claim 1 wherein each of the fasteners is a one-piece tissue fastener comprising:
a tubular body having proximal and distal ends; a plurality of proximal legs extending from the proximal end of the body and a plurality of distal legs extending from the distal end of the body, the body and the legs being formed from a shape memory material, the legs having an unstressed deployed configuration in which they extend radially outward from the body, the legs being bendable from their unstressed configuration to a low profile, stressed configuration in which the legs extend in a more longitudinally oriented direction so that they can be contained within a tubular delivery device; the fastener being adapted to engage and secure together multiple layers of tissue with the tubular body transfixing the tissue layers and the tissue layers contained between the deployed proximal legs and the deployed distal legs.

\* \* \* \* \*